(12) United States Patent
Lechmann et al.

(10) Patent No.: US 8,313,529 B2
(45) Date of Patent: Nov. 20, 2012

(54) TOTAL DISC REPLACEMENT WITH W-SHAPED SPRING ELEMENTS

(75) Inventors: Beat Lechmann, Grenchen (CH); Silas Zurschmiede, Grenchen (CH); Cyril Voisard, Niederbipp (CH)

(73) Assignee: Synthes USA, LLC, West Chester, PA (US)

( * ) Notice: Subject to any disclaimer, the term of this patent is extended or adjusted under 35 U.S.C. 154(b) by 270 days.

(21) Appl. No.: 12/674,807

(22) PCT Filed: Feb. 22, 2010

(86) PCT No.: PCT/US2010/024921
§ 371 (c)(1),
(2), (4) Date: Feb. 23, 2010

(87) PCT Pub. No.: WO2011/102843
PCT Pub. Date: Aug. 25, 2011

(65) Prior Publication Data
US 2011/0208307 A1  Aug. 25, 2011

(51) Int. Cl.
*A61F 2/44* (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| | | |
|---|---|---|
| 4,309,777 A | 1/1982 | Patil |
| 4,759,769 A | 7/1988 | Hedman et al. |
| 5,011,497 A | 4/1991 | Persson et al. |
| 5,062,851 A | 11/1991 | Branemark |
| 5,092,866 A | 3/1992 | Breard et al. |
| 5,123,926 A | 6/1992 | Pisharodi |
| 5,180,381 A | 1/1993 | Aust et al. |
| 5,180,393 A | 1/1993 | Commarmond |
| 5,387,213 A | 2/1995 | Breard et al. |
| 5,395,372 A | 3/1995 | Holt et al. |

(Continued)

FOREIGN PATENT DOCUMENTS

AU       0650620 B2    11/1991

(Continued)

OTHER PUBLICATIONS

Rousseau et al "The instant axis of rotation influences facet forces at L5/S1 during flexion/extension and lateral bending" Eur Spine J., vol. 15, pp. 299-307 (2006).

(Continued)

*Primary Examiner* — Ellen C Hammond
(74) *Attorney, Agent, or Firm* — Woodcock Washburn LLP

(57) ABSTRACT

An intervertebral implant for mounting between superior and inferior vertebrae includes first and second endplates and an inlay. The first endplate has a first vertebra engagement surface and a first inner surface. The first vertebra engagement surface is mounted to the superior vertebra in an implant positions. The second endplate has a second vertebra engagement surface and a second inner surface. The second vertebra engagement surface is mounted to the inferior vertebra in the implanted position. The inlay is mounted to and between the first and second inner surfaces in an assembled configuration. The inlay includes a first mounting plate, a second mounting plate, a first W-shaped spring and a second W-shaped spring. The first and second W-shaped springs are mounted between the first and second mounting plates. The first and second W-shaped springs have longitudinal axes that are generally parallel to the insertion axis.

17 Claims, 4 Drawing Sheets

U.S. PATENT DOCUMENTS

| | | |
|---|---|---|
| 5,415,661 A | 5/1995 | Holmes |
| 5,458,642 A | 10/1995 | Beer et al. |
| 5,496,318 A | 3/1996 | Howland et al. |
| 5,507,823 A | 4/1996 | Walston et al. |
| 5,645,599 A | 7/1997 | Samani |
| 5,674,296 A | 10/1997 | Bryan et al. |
| 5,676,702 A | 10/1997 | Ratron |
| 5,827,328 A | 10/1998 | Buttermann |
| 5,879,396 A | 3/1999 | Walston et al. |
| 5,928,284 A | 7/1999 | Mehdizadeh |
| 6,231,609 B1 | 5/2001 | Mehdizadeh |
| 6,440,169 B1 | 8/2002 | Elberg et al. |
| 6,475,219 B1 | 11/2002 | Shelokov |
| 6,520,996 B1 | 2/2003 | Manasas et al. |
| 6,572,653 B1 | 6/2003 | Simonson |
| 6,743,257 B2 | 6/2004 | Castro |
| 6,758,861 B2 | 7/2004 | Ralph et al. |
| 6,770,094 B2 | 8/2004 | Fehling et al. |
| 6,802,867 B2 | 10/2004 | Manasas et al. |
| 6,869,446 B2 | 3/2005 | Ralph et al. |
| 6,936,071 B1 | 8/2005 | Marnay et al. |
| 6,966,910 B2 | 11/2005 | Ritland |
| 7,052,515 B2 | 5/2006 | Simonson |
| 7,083,649 B2 * | 8/2006 | Zucherman et al. ....... 623/17.11 |
| 7,238,204 B2 | 7/2007 | Le Couedic et al. |
| 2003/0083749 A1 | 5/2003 | Kuslich et al. |
| 2004/0024461 A1 | 2/2004 | Ferree |
| 2004/0181284 A1 | 9/2004 | Simonson |
| 2004/0225361 A1 | 11/2004 | Glenn et al. |
| 2004/0249462 A1 | 12/2004 | Huang |
| 2004/0249463 A1 | 12/2004 | Bindseil et al. |
| 2005/0125063 A1 | 6/2005 | Matge et al. |
| 2005/0203624 A1 | 9/2005 | Serhan et al. |
| 2005/0251260 A1 | 11/2005 | Gerber et al. |
| 2006/0200243 A1 | 9/2006 | Rothman et al. |
| 2007/0168033 A1 | 7/2007 | Kim et al. |
| 2007/0191958 A1 | 8/2007 | Abdou |
| 2007/0225806 A1 | 9/2007 | Squires et al. |
| 2008/0140203 A1 | 6/2008 | Davis |
| 2008/0154381 A1 | 6/2008 | Parrish |
| 2008/0161924 A1 | 7/2008 | Viker |
| 2008/0167686 A1 | 7/2008 | Trieu et al. |
| 2008/0177389 A1 | 7/2008 | Parrish |
| 2009/0076614 A1 | 3/2009 | Arramon |
| 2009/0112326 A1 | 4/2009 | Lehuec et al. |
| 2009/0138085 A1 | 5/2009 | Simonson |
| 2009/0157185 A1 | 6/2009 | Kim |
| 2009/0192617 A1 * | 7/2009 | Arramon et al. ............ 623/17.16 |
| 2010/0204732 A1 * | 8/2010 | Aschmann et al. ........... 606/249 |
| 2011/0071636 A1 * | 3/2011 | Tsuang et al. ............. 623/17.13 |

FOREIGN PATENT DOCUMENTS

| | | |
|---|---|---|
| DE | 3113142 A1 | 1/1982 |
| DE | 4315757 C1 | 11/1994 |
| EP | 0322334 A1 | 6/1989 |
| EP | 1273276 A2 | 1/2003 |
| FR | 2681525 A1 | 3/1993 |
| FR | 2812806 A1 | 2/2002 |
| RU | 2077288 C1 * | 4/1997 |
| SU | 1484348 A1 | 6/1989 |
| WO | WO 9426213 * | 3/1994 |
| WO | WO 94/26213 | 11/1994 |
| WO | 0162190 A1 | 8/2001 |
| WO | 2005032432 A1 | 4/2005 |
| WO | 2005094732 A1 | 10/2005 |
| WO | 2005094733 A1 | 10/2005 |
| WO | 2008088777 A2 | 7/2008 |
| WO | 2008091112 A1 | 7/2008 |
| WO | WO 2009/129605 A1 | 10/2009 |

OTHER PUBLICATIONS

Pearcy et al. "Instantaneous Axes of Rotation of the Lumbar Intervertebral Joints" Spine , vol. 13 , No. 9, pp. 1033-1041 (1988).

Huang et al. "The Implications of Constraint in Lumbar Total Disc Replacement" Journal of Spinal Disorders & Techniques, vol. 16, No. 4, pp. 412-417 (2003).

Gertzbein et al."Centrode Patterns and Segmental Instability in Degenerative Disc Disease" Spine, vol. 10, No. 3 pp. 207-261 (1985).

Freudiger et al. "Dynamic neutralisation of the lumbar spine confirmed on a new lumbar spine simulator in vitro" Original Article (May 4, 1998).

Baumgartner, Walter Rolf "Die Bewegungen Einzelner Lendenwirbel Unter Alltagsbelastungen" (Mar. 1951).

* cited by examiner

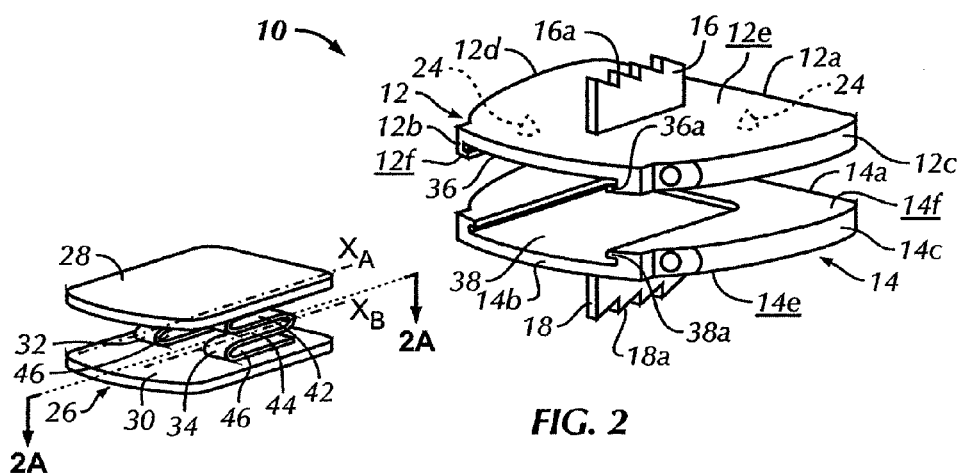
FIG. 2
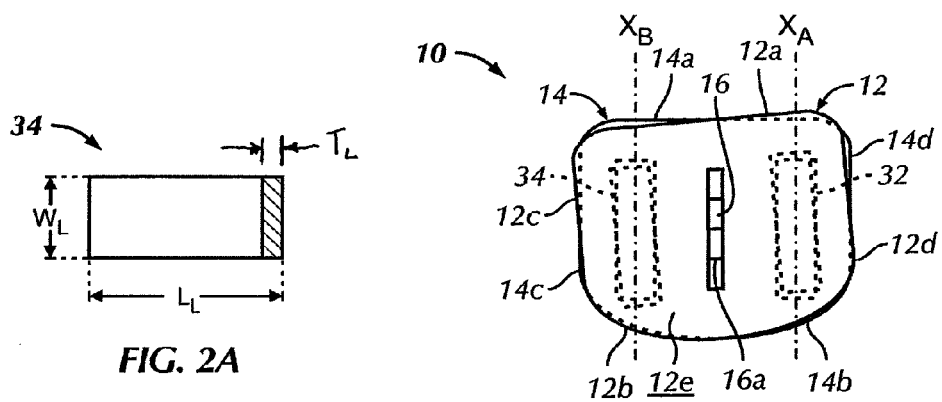
FIG. 2A
FIG. 3

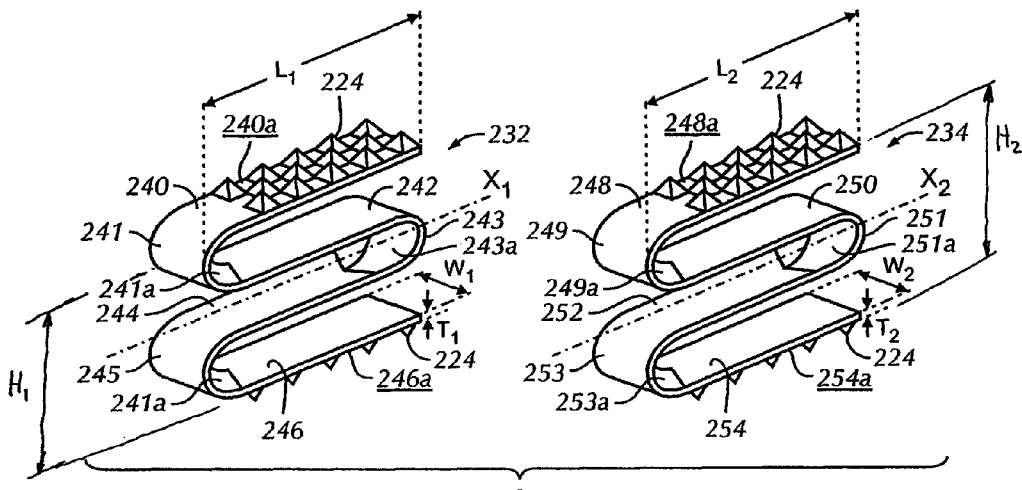
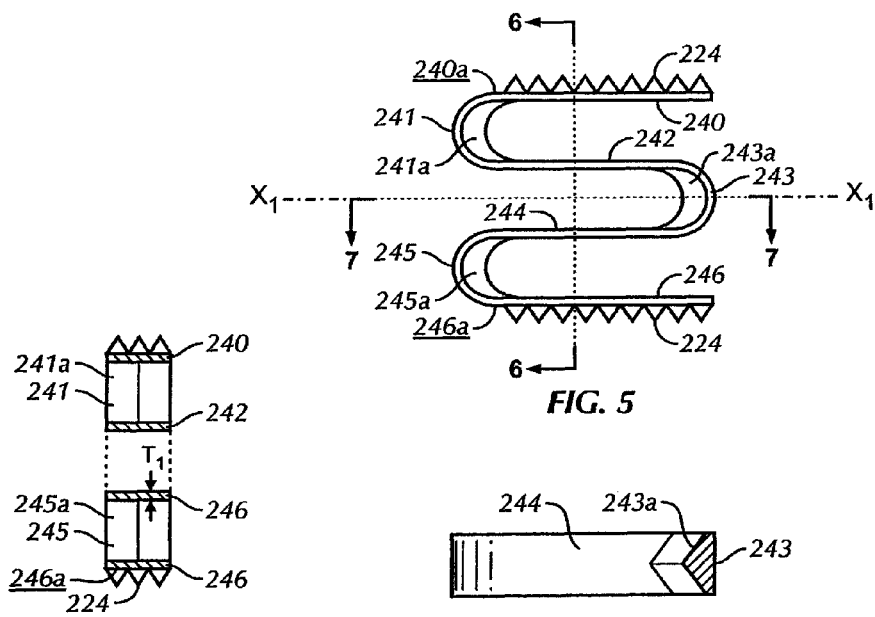
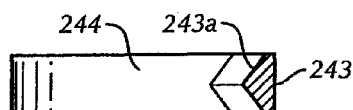

TOTAL DISC REPLACEMENT WITH W-SHAPED SPRING ELEMENTS

CROSS-REFERENCE TO RELATED APPLICATIONS

This application is a section 371 of International Application No. PCT/US2010/24921, filed Feb. 22, 2010, the disclosure of which is incorporated herein by reference.

BACKGROUND

Motion preservation intervertebral implants for use in spinal surgery are utilized to preserve motion at the motion segment that is impacted by the surgery. Typical motion preservation devices do not replicate the anatomical motions and reactions of an intervertebral disc. Specifically, certain implants restrict most motions at the impacted level to a limited amount of pivoting or pitching between the vertebrae. It is desirable to design and construct an intervertebral motion preservation implant that mimics physiological or anatomical motion of an intervertebral disc to repair a diseased or damaged disc to its original, anatomical dampening and motion limitations.

BRIEF SUMMARY

Briefly stated, one exemplary embodiment is directed to an intervertebral implant for mounting between a superior vertebra and an inferior vertebra including a first endplate, a second endplate and an inlay. The first endplate has a first leading end, a first trailing end, a first lateral side, a second lateral side, a first vertebra engagement surface and a first inner surface. The first vertebra engagement surface is mounted to the superior vertebra in an implanted position. The second endplate has a second leading end, a second trailing end, a third lateral side, a fourth lateral side, a second vertebra engagement surface and a second inner surface. The second vertebra engagement surface is mounted to the inferior vertebra in the implanted position. The inlay is mounted to and between the first and second inner surfaces in an assembled configuration. The inlay includes a first mounting plate, a second mounting plate, a first W-shaped spring and a second W-shaped spring. The first and second W-shaped springs are mounted between the first and second mounting plates on opposite sides of an insertion plane. The first and second W-shaped springs have longitudinal axes that are oriented generally parallel to the insertion axis.

Another exemplary embodiment is directed to an intervertebral implant system for mounting between a superior vertebra and an inferior vertebra that define a sagital plane via a posterior approach. The orientation of the posterior approach is generally parallel to the sagital plane. The intervertebral implant system includes a first W-shaped spring and a second W-shaped spring. The first W-shaped spring includes first, second, third and fourth legs. The first leg has a first vertebra engagement surface and the fourth leg has a second vertebra engagement surface. The first and second vertebra engagement surfaces face away from each other. The first W-shaped spring has a first length, a first width and a first thickness. The first length is greater than the first width and the first width is greater than the first thickness. The second W-shaped spring has fifth, sixth, seventh and eighth legs. The fifth leg has a third vertebra engagement surface and the eighth leg has a fourth vertebra engagement surface. The third and fourth vertebra engagement surfaces face away from each other. The second W-shaped spring has a second length, a second width and a second thickness. The first and third vertebra engagement surfaces contact the superior vertebra and the second and fourth vertebra engagement surfaces contact the inferior vertebra in an implanted position.

BRIEF DESCRIPTION OF THE SEVERAL VIEWS OF THE DRAWINGS

The foregoing summary, as well as the following detailed description will be better understood when read in conjunction with the appended drawings. For the purpose of illustration, various exemplary embodiments are described, however, it should be understood that the invention is not limited to the precise arrangements and instrumentalities shown. In the drawings:

FIG. 2 is a rear perspective, partially exploded view of the intervertebral implant of FIG. 1;

FIG. 2A is a cross-sectional view of a second W-shaped spring of the intervertebral implant of FIG. 1, taken along line 2A-2A of FIG. 2;

FIG. 3 is a top plan view of the intervertebral implant of FIG. 1, shown in a twisted configuration about a vertical axis;

FIG. 4 is a front perspective view of first and second W-shaped springs of an intervertebral implant system in accordance with a second exemplary embodiment;

FIG. 5 is a side elevational view of the first W-shaped spring of FIG. 4;

FIG. 6 is a cross-sectional view of the first W-shaped spring of FIG. 4, taken along line 6-6 of FIG. 5;

FIG. 7 is a cross-sectional, partial fragmentary view of the first W-shaped spring of FIG. 4 taken along line 7-7 of FIG. 5.

DETAILED DESCRIPTION

Figure 1:
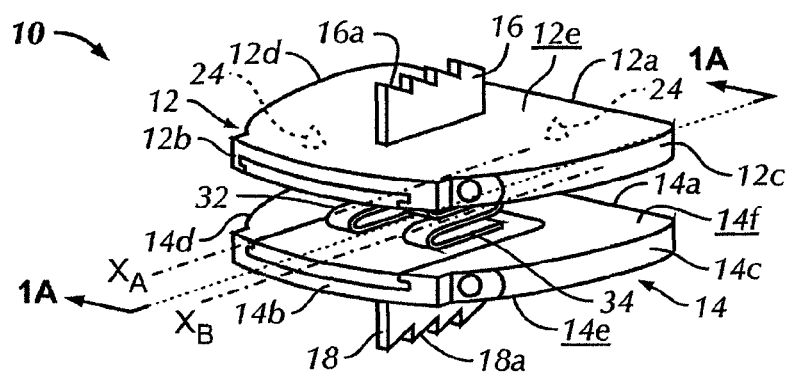
FIG. 1 is a rear perspective view of an intervertebral implant in accordance with a first exemplary embodiment.

Certain terminology is used in the following description for convenience only and is not limiting. The words "right," "left," "lower," and "upper" designate directions in the drawings to which reference is made. The words "inwardly" or "distally" and "outwardly" or "proximally" refer to directions toward and away from, respectively, the geometric center of the exemplary implants and instruments and related parts thereof. The words, "anterior," "posterior," "superior," "inferior," "lateral," "medial," and related words and/or phrases designate preferred positions and orientations in the human body to which reference is made and are not meant to be limiting. The terminology includes the above-listed words, derivatives thereof and words of similar import.

Referring to FIGS. 1-3, in a first exemplary embodiment, an intervertebral implant 10 for mounting between a superior vertebra $V_S$ and an inferior vertebra $V_I$ is comprised of a total disc replacement implant 10 that permits motion in six degrees of freedom between the superior and inferior vertebra $V_S$, $V_I$ following surgery. Accordingly, motion between the superior and inferior vertebra $V_S$, $V_I$ is preserved in comparison to a typical fusion surgery wherein motion between the vertebrae $V_S$, $V_I$ is eliminated.

Figure 1A:
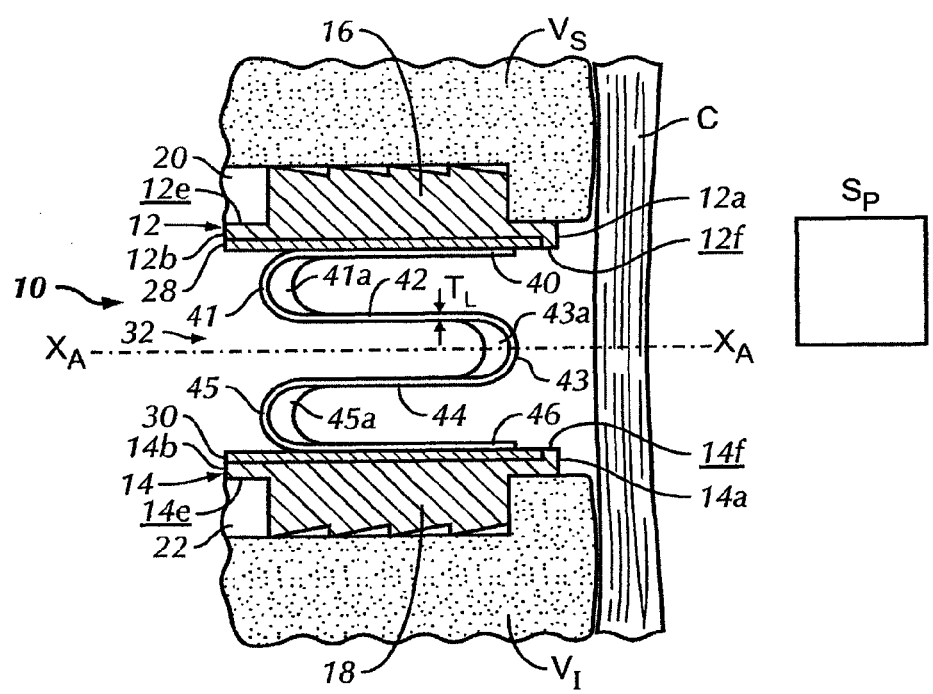
FIG. 1A is a cross-sectional view of the implant of FIG. 1, taken along line 1A-1A of FIG. 1 and shown mounted between a superior vertebra and an inferior vertebra in an implanted position.
Figure 8:
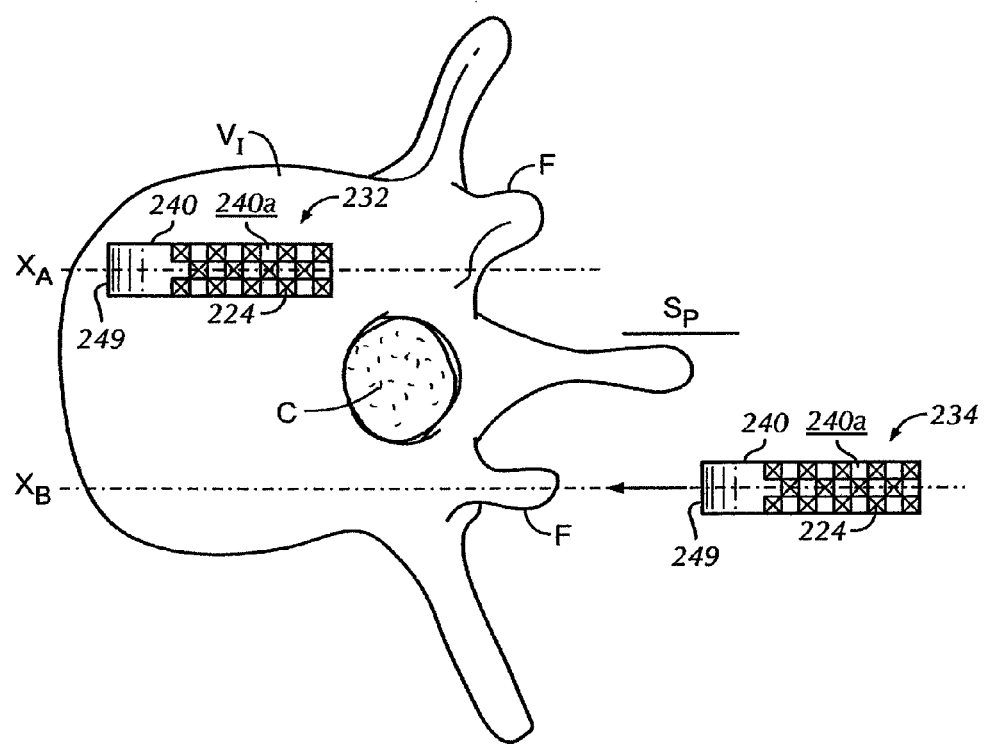
FIG. 8 is a top plan view of the first and second W-shaped springs of FIG. 4 of the intervertebral implant system of the second exemplary embodiment, shown implanted or positioned to be implanted between superior and inferior vertebrae.

The intervertebral implant 10 of the first exemplary embodiment includes a first endplate 12 having a first leading end 12a, a first trailing end 12b, a first lateral side 12c, a second lateral side 12d, a first vertebra engagement surface 12e and a first inner surface 12f. The intervertebral implant 10 of the first exemplary embodiment also includes a second endplate 14 having a second leading end 14a, a second trailing end 14b, a third lateral side 14c, a fourth lateral side 14d, a second vertebra engagement surface 14e and a second inner surface 14f. The first vertebra engagement surface 12e is mounted to the superior vertebra $V_S$ and the second vertebra engagement surface 14e is mounted to the inferior vertebra $V_I$ in an implanted position (FIG. 1A). When viewed from the top, the first and second endplates 12, 14 have the same peripheral, generally rectangular shape, wherein the trailing end 12b, 14b is arcuate. The first and second endplates 12, 14 are not limited to having the above-described shape and each of the leading ends 12a, 14a, trailing ends 12b, 14b and lateral sides 12c, 12d, 14c, 14d may be generally straight, curved, arcuate, wavy or have nearly any shape. However, the first and second endplates 12, 14 are shaped to contact a peripheral rim of the vertebral bodies of the vertebrae $V_S$, $V_I$ that the endplates 12, 14 are mounted to in an implanted position. Positioning of the leading ends 12a, 14a, trailing ends 12b, 14b and lateral sides 12c, 12d, 14c, 14d proximate the peripheral rim or cortical rim of the vertebral bodies of the superior and inferior vertebra $V_S$, $V_I$ provides a relatively strong, secure engagement between the implant 10 and the vertebrae $V_S$, $V_I$. These portions of the implant 10 may be positioned adjacent the relatively strong peripheral rim to limit subsistence and securely attach the implant 10 to the vertebra $V_S$, $V_I$.

The first endplate 12 includes a first keel 16 extending generally perpendicularly from the first vertebra engagement surface 12e and the second endplate 14 includes a second keel 18 extending generally perpendicularly from the second vertebra engagement surface 14e. The first and second keels 16, 18 extend along a substantial portion of the first and second vertebra engagement surfaces 12e, 14e, generally longitudinally between the leading ends 12a, 14a and the trailing ends 12b, 14b. The first and second keels 16, 18 preferably extend generally coplanar with an insertion axis A-A of the implant 10 in an assembled configuration.

The first and second keels 16, 18 also include serrated teeth or a serrated edge 16a, 18a on their top surfaces. The serrated teeth 16a, 18a accommodate insertion of the keels 16, 18 into a superior keel cut 20 and an inferior keel cut 22 (respectively, during implantation). The points of the serrated teeth 16a, 18a generally point towards the trailing ends 12b, 16b to accommodate insertion of the endplates 12, 14 but to resist expulsion of the intervertebral implant 10 from the disc space in the implanted position. The first and second endplates 12, 14 are not limited to including the first and second keels 16, 18 having the serrated teeth 16a, 18a and may be secured to the superior and inferior vertebrae $V_S$, $V_I$ utilizing spikes, fastening, adhesive bonding, clamping or other techniques to secure the first and second endplates 12, 14 to the vertebrae $V_S$, $V_I$.

Specifically, the first and second endplates 12, 14 may be secured to the superior and inferior vertebrae $V_S$, $V_I$ utilizing spikes 24 (shown in phantom line type). The spikes 24 may be utilized in combination with the first and second keels 16, 18 or by themselves to secure the first and second endplates 12, 14 to the vertebrae $V_S$, $V_I$. The spikes 24 extend into the endplates of the vertebrae $V_S$, $V_I$ to provide primary fixation of the endplates 12, 14 to the vertebrae $V_S$, $V_I$.

The intervertebral implant 10 of the first exemplary embodiment also includes an inlay 26 mounted to and between the first and second inner surfaces 12f, 14f in an assembled configuration (FIGS. 1, 1A and 3). The inlay 26 includes a first mounting plate 28, a second mounting plate 30, a first W-shaped spring 32 and a second W-shaped spring 34. The first and second mounting plates 28, 30 are positioned within first and second cavities 36, 38, respectively, defined in the first and second inner surfaces 12f, 14f of the first and second endplates 12, 14. The first and second cavities 36, 38 include rails 36a, 38a along their side edges that retain the edges of the first and second mounting plates 28, 30 therein and guide the first and second mounting plates 28, 30 into the assembled configuration. The first and second mounting plates 28, 30 are retained in the first and second cavities 36, 38 in the assembled configuration by a snap-fit, press-fit, fastening mechanisms, clamping mechanisms or some other similar securing mechanism that is able to retain the first and second mounting plates 28, 30 in the first and second cavities 36, 38 in the assembled configuration.

The first and second W-shaped springs 32, 34 include first, second, third and fourth legs 40, 42, 44, 46, respectively. The first, second, third and fourth legs 40, 42, 44, 46 have a leg length $L_L$, a leg width $W_L$ and a leg thickness $T_L$. Each of the legs 40, 42, 44, 46 of the first and second W-shaped springs 30, 34 has the same leg length $L_L$, leg width $W_L$ and leg thicknesses $T_L$. The leg length $L_L$ is greater than the leg width $W_L$ and the leg width $W_L$ is greater than the leg thickness $T_L$ in the first exemplary embodiment. However, the first and second W-shaped springs 32, 34 are not so limited and may have differences in their leg lengths $L_L$, leg widths $W_L$ and leg thicknesses $T_L$ between the first and second W-shaped springs 32, 34 and/or between the individual legs 40, 42, 44, 46 to adapt the properties of the first and second W-shaped springs 32, 34 and/or the intervertebral implant 10 to a specific portion of a patient's spine or to a specific condition that is being treated.

The leg length $L_L$ is approximately five to thirteen millimeters (5-13 mm), the leg width $W_L$ is approximately one to four millimeters (1-4 mm) and the leg thickness $T_L$ is approximately two tenths to eight tenths of a millimeter (0.2-0.8 mm) in the first exemplary embodiment of the intervertebral implant 10 that is adapted for mounting in a lumbar region of patient's spine. The first and second W-shaped springs 32, 34 are not limited to having the above-listed leg length $L_L$, leg width $W_L$ and leg thickness $T_L$ and may be sized and configured to adapt the properties of the first and second W-shaped springs 32, 34 for various anatomical situations or generally to a designer's preferences. However, the first, second, third and fourth legs 40, 42, 44, 46 have generally consistent leg lengths $L_L$, leg widths $W_L$ and leg thicknesses $T_L$ such that the properties of the first and second W-shaped springs 32, 34 are substantially similar and consistent, although for various reasons, their properties could be designed to be different.

In the first exemplary embodiment, the first legs 40 are secured to the first mounting plate 28 and the fourth legs 46 are secured to the second mounting plate 30 for both the first and second W-shaped springs 32, 34. The first and fourth legs 40, 46 may be fastened, adhesively bonded, integrally formed, clamped or otherwise mounted and secured to the first and second mounting plates 28, 30, respectively. Alternatively, the first and second W-shaped springs 32, 34 may be removably mounted to the first and second mounting plates 28, 30 such that the springs 32, 34 may be removed and replaced with alternative springs having different properties such that the implant 10 may be adapted for implantation into different portions of the patient's spine or to address different conditions of the patient's spine. For example, first and second W-shaped springs 32, 34 having a high stiffness may be mounted to the first and second mounting plates 28, 30 for implantation into a lumbar region of a patient's spine, while first and second W-shaped springs 32, 34 having a relatively lower stiffness may be mounted to the first and second plates 28, 30 for implantation into the cervical portion of a patient's spine.

A first inflection 41 is defined by the first and second legs 40, 42, a second inflection 43 is defined by the second and third legs 42, 44 and a third inflection 45 is defined by the third and fourth legs 44, 46. The first, second and third inflections 41, 43, 45 have a U-shape and are formed at the intersection of the respective legs 40, 42, 44, 46. The inflections 41, 43, 45 are not limited to having U-shapes and may take on nearly any shape that permits transition between the legs 40, 42, 44, 46 and provides a structure of the first and second W-shaped springs 32, 34 that permits damped movement between the first and second mounting plates 28, 30.

The first, second and third inflections 41, 43, 45 of the first exemplary embodiment include a stiffening member 41a, 43a, 45a. The stiffening members 41a, 43a, 45a provide strength and stiffness at the inflections 41, 43, 45 to reduce the potential for breakage or fatigue failure at the stiffening members 41a, 43a, 45a. The first and second W-shaped springs 32, 34 are not limited to including the stiffening members 41a, 43a, 45a at the inflections 41, 43, 45 and may be designed and configured to exclude the stiffening members 41a, 43a, 45a, without significantly limiting or modifying the performance of the first and second W-shaped springs 32, 34. However, the stiffening members 41a, 43a, 45a typically permit tailoring of the properties of the first and second W-shaped springs 32, 34 and to provide strength and stiffness at the inflections 41, 43, 45.

In the first exemplary embodiment, the first and second W-shaped springs 32, 34 are constructed of a metallic material that is relatively stiff and strong and is biocompatible. For example, the W-shaped springs 32, 34 may be constructed of Titanium, stainless steel or other metallic materials. The metallic material permits damped movement between the first and second mounting plates 28, 30 when constructed, as is shown in FIGS. 1-3. However, the first and second W-shaped springs 32, 34 are not limited to metallic constructions and may be constructed of a polymeric or other relatively strong, stiff, biocompatible material that is able to take on the general size and shape of the W-shaped springs 32, 34 and withstand the normal operating conditions of the W-shaped springs.

The first and second W-shaped springs 32, 34 are mounted between the first and second mounting plates 28, 30 on opposite sides of the insertion axis A-A in the first exemplary embodiment. The first and second W-shaped springs 32, 34 have longitudinal axes $X_A$, $X_B$, respectively, that are oriented generally parallel to the insertion axis A-A in the implanted position.

The intervertebral implant 10 of the first exemplary embodiment may be constructed such that all of its components are comprised of a metal material. For example, the first and second endplates 12, 14 and the inlay 26 are constructed of metallic materials. The metallic construction of the intervertebral implant 10 of the first exemplary embodiment provides a relatively simple implant that is able to be repeatedly manufactured with know processes and techniques. The metallic construction also permits biocompatible constructions utilizing known materials and generally eliminates corrosion or degradation resulting from the combination of dissimilar materials in a single implant.

In use, a damaged vertebral disc is removed from the spine, the superior keel cut 20 is formed in the superior vertebra $V_S$ and the inferior keel cut 22 is formed in the inferior vertebra $V_I$. The first and second endplates 12, 14 are positioned such that the first and second inner surfaces 12f, 14f are in contact or close proximity to each other and the first and second keels 16, 18 are generally aligned for insertion into the superior and inferior keel cuts 20, 22, respectively. A tool (not shown) inserts the endplates 12, 14 into the prepared disc space such that the first and second keels 16, 18 are positioned in the superior and inferior keel cuts 20, 22, respectively. The first and second endplates 12, 14 are distracted toward the superior and inferior vertebrae $V_S$, $V_I$ such that the serrated teeth 16a, 18a are driven into the vertebrae $V_S$, $V_I$ and the first and second cavities 36, 38 are separated to provide a space for insertion of the inlay 26. The inlay 26 is typically implanted with a tool (not shown) such that the lateral edges of the first and second mounting plates 28, 30 are engaged by the first and second rails 36a, 38a. When fully inserted, the first and second mounting plates 28, 30 are locked to the first and second endplates 12, 14, respectively. The patient's incision is closed and the total disc replacement, motion preservation implant 10 of the first exemplary embodiment permits six degrees of freedom of motion between the superior and inferior vertebrae $V_S$, $V_I$.

The inclusion of the first and second W-shaped springs 32, 34 in the inlay 26 releases constraints between the first and second mounting plates 28, 30 and the first and second endplates in comparison to certain commercially available total disc replacement motion preservation implants. The first and second W-shaped springs 32, 34 of the first exemplary total disc replacement motion preservation implant 10 allow super-posed or coupled motions between the superior and inferior vertebrae $V_S$, $V_I$ that are generally closer to anatomical motions and may be more forgiving to surrounding anatomical structures following surgery. Accordingly, the intervertebral implant 10 of the first exemplary embodiment is better able to mimic the physiological reality of the spine. Specifically, the natural disc does not include mechanical constraints that inhibit certain of the motions of the six degrees of freedom and the natural disc does not include a specific center of rotation. The first exemplary implant 10 comprises the above-described full metallic construction that permits coupled motions and a more anatomically correct motion when compared to conventional commercially available devices. Specifically, implant 10, including the first and second W-shaped springs 32, 34, permit relatively anatomical motion at the facet joints 20 following implantation, particularly during lateral bending, as the superior and inferior vertebrae $V_S$, $V_I$ are generally able to move in six-degrees of freedom relative to each other following implantation of implant 10.

Referring to FIGS. 4-8, an intervertebral implant system 210 in accordance with a second exemplary embodiment includes first and second W-shaped springs 232, 234. The first and second W-shaped springs 232, 234 of the second exemplary embodiment are similar to the first and second W-shaped spring 32, 34 of the first exemplary embodiment and like reference numerals will be utilized to describe the features of the first and second W-shaped springs 232, 234 of the second exemplary embodiment with the prefix, "2" to specifically identify the components or features of the second exemplary embodiment. The first and second W-shaped springs 232, 234 are configured for mounting between the superior and inferior vertebrae $V_S$, $V_I$ via a posterior approach and generally along a plane that is parallel to a sagittal plane $S_P$.

The first W-shaped spring 232 includes first, second, third and fourth legs 240, 242, 244, 246 and the second W-shaped spring 234 includes fifth, sixth, seventh and eighth legs 248, 250, 252, 254, respectively.

The first leg 240 has a first vertebra engagement surface 240a and the fourth leg 246 has a second vertebra engagement surface 246a. The first and second vertebra engagement surfaces 240a, 246a face away from each other such that they are able to contact the superior and inferior vertebra $V_S$, $V_I$, respectively, in the implanted position.

The first W-shaped spring 232 has a first length $L_1$, a first width $W_1$ and a first thickness $T_1$. The first length $L_1$ is greater than the first width $W_1$ and the first width $W_1$ is greater than the first thickness $T_1$. The first, second, third and fourth legs 240, 242, 244, 246 each preferably have the same first length $L_1$, first width $W_1$ and first thickness $T_1$, but are not so limited. For example, the individual legs 240, 242, 244, 246 may have different first lengths $L_1$, first widths $W_1$ or first thicknesses $T_1$ to influence the properties of the first spring 240. However, in the second exemplary embodiment, the individual legs 240, 242, 244, 246 have nearly identical structures to ease manufacturability and provide a relatively consistent first spring 240.

The second W-shaped spring 234 typically has an identical construction to the first W-shaped spring 232 in the second exemplary embodiment but is not so limited. For example, the second W-shaped spring 234 may have modified spring characteristics resulting from a different construction or constructions using a different material to provide different reaction to forces encountered in the implanted position. However, the second W-shaped spring 234 typically has an identical construction to the first W-shaped spring 232 to provide a consistent support and reaction to forces in the implanted position, as will be described in greater detail below.

The fifth leg 248 has a third vertebra engagement surface 248a and the eighth leg 254 has a fourth vertebra engagement surface 254a. The third vertebra engagement surface 248a preferably contacts the superior vertebra $V_S$ and the fourth vertebra engagement surface 254a preferably contacts the inferior vertebra $V_I$ in the implanted position. In addition, the third and fourth vertebra engagement surfaces 248a, 254a face away from each other.

The second W-shaped spring 234 has a second length $L_2$, a second width $W_2$ and a second thickness $T_2$. Similar to the first W-shaped spring 232, the second length $L_2$, the second width $W_2$ and the second thickness $T_2$ of the second W-shaped spring 234 are not limited to being equivalent to the same features of the fifth, sixth, seventh and eighth legs 248, 250, 252, 254 and the individual legs 248, 250, 252, 254 may be varied in size and shape to tailor the properties of the second W-shaped spring 234.

In the second exemplary embodiment, the first and second lengths $L_1$, $L_2$ are approximately sixteen to twenty-four millimeters (16-24 mm), the first and second widths $W_1$, $W_2$ are approximately four to nine millimeters (4-9 mm) and the first and second thicknesses $T_1$, $T_2$ are approximately six tenths to one and two tenths millimeters (0.6-1.2 mm) when the first and second W-shaped springs 232, 234 are adapted for implantation into a patient's lumbar spine. Exemplary first and second W-shaped springs 232, 234 of the second exemplary embodiment have first and second lengths $L_1$, $L_2$ of twenty millimeters (20 mm), first and second widths $W_1$, $W_2$ of five millimeters (5 mm) and first and second thicknesses $T_1$, $T_2$ of eight tenths of a millimeter (0.8 mm). The first and second W-shaped springs 232, 234 are not limited to the above-listed dimensions and may have alternate dimensions or be adapted for various other sections of the spine or body, such as the cervical spine, resulting in dimensions that fall outside of the above-described ranges, which are generally preferable for lumbar spine constructions.

The first and second W-shaped springs 232, 234 of the second exemplary embodiment also have first and second spring heights $H_1$, $H_2$ that are adapted for insertion into a prepared disc space to restore a generally anatomic disc height between two adjacent vertebrae $V_S$, $V_I$. The spring heights $H_1$, $H_2$ of the second exemplary embodiment are approximately five to thirteen millimeters (5-13 mm) when the springs 232, 234 are adapted for the lumbar spine, but are not so limited and may be adapted to have nearly any spring height that is able to generally restore the anatomical height between the adjacent vertebrae $V_S$, $V_I$. In addition, the first and second W-shaped springs 232, 234 may be adapted for implantation into various other parts of a patient's body, such as the cervical spine, and may have first and second spring heights $H_1$, $H_2$ that fall outside of the above-described ranges to adapt the first and second W-shaped springs 232, 234 to particular anatomical features of the patient's body.

A first stiffening member 241a is positioned at a first inflection 241 defined by the first and second legs 240, 242. The first stiffening member 241a is integrally formed with the first W-shaped spring 232 and is positioned at an inner surface of the U-shaped first inflection 241. The first stiffening member 241a is not limited to being integrally formed with the first W-shaped spring 30 232 and may be subsequently mounted to or removably mounted to the first inflection 241, inside or outside of the U-shaped first inflection 241, without significantly impacting the operation of the first W-shaped spring 232.

The first and second W-shaped springs 232, 234 also include a second stiffening member 243a defined at a second inflection 243, a third stiffening member 245a defined at a third inflection 245, a fourth stiffening member 249a defined at a fourth inflection 249, a fifth stiffening member 251a defined at a fifth inflection 251 and a sixth stiffening member 252a defined at a sixth inflection 2253. The first and second W-shaped springs 232, 234 are not limited to inclusion of the stiffening members 241a, 243a, 245a, 249a, 251a, 252a, but the components may tailor the features of the first and second W-shaped springs 232, 234, to provide strength and stiffness at the inflections 241, 243, 245, 249, 251, 253 and to tailor the properties of the first and second W-shaped springs 232, 234.

In the second exemplary embodiment, the first, third, fourth and sixth stiffening members 241a, 245a, 249a, 253a are positioned proximate a leading end of the first and second W-shaped springs 232, 234, respectively. In addition, the second stiffening member 243a, and the fifth stiffening member 251a are positioned proximate a trailing end of the first and second W-shaped springs 232, 234, respectively. Such a configuration permits insertion of the first and second W-shaped springs 232, 234 with the blunt end of the first, third, fourth and sixth inflections 241, 245, 249, 243 initially into the disc space between the superior and inferior vertebrae $V_S$, $V_I$. Such a configuration permits relatively smooth insertion into the disc space without sharp edges impacting the vertebrae $V_S$, $V_I$. The first and second W-shaped springs 232, 234 are not limited to inclusion of the stiffening members 241a, 243a, 245a, 249a, 251a, 253a.

The first, second, third and fourth vertebra engagement surfaces 240a, 246a, 248a, 254a preferably include fixation mechanisms or spikes 224 extending therefrom. The spikes 224 may have a serrated configuration to promote insertion into the disc space, similar to the serrated teeth 16a, 18a of the first and second keels 16, 18, may have a pyramidal-shape, conical-shape or nearly any shape that permits an promotes engagement between the first, second, third and fourth vertebra engagement surfaces 240a, 246a, 248a, 254a with the endplates of the superior and inferior vertebrae $V_S$, $V_I$ in the implanted position. Spikes 224 are positioned in the endplates in the implanted position to provide primary fixation and limit movement of the first, second, third and fourth vertebra engagement surfaces 240a, 246a, 248a, 254a relative to the superior and inferior vertebrae $V_S$, $V_I$ when implanted and during use.

The first W-shaped spring 232 defines a first longitudinal axis $X_1$ and the second W-shaped spring 234 defines a second longitudinal axis $X_2$. The first and second longitudinal axes $X_1$, $X_2$ are oriented generally parallel to the sagital plane $S_p$ in the implanted position. The first and second longitudinal axis $X_1$, $X_2$ are not limited to being oriented generally parallel to the sagital plane $S_p$ in the implanted position and may be oriented at an angle with respect to the sagital plane $S_p$ such that the first and second W-shaped springs 232, 234 are easier to implant around the spinal cord C, to provide different spring and damping characteristics in the implanted position or to otherwise engage the superior and inferior vertebrae $V_S$, $V_I$ at desired locations.

In use, the first and second W-shaped springs 232, 234 of the second exemplary embodiment are implanted in the disc space between the superior and inferior vertebrae $V_S$, $V_I$ via a posterior or posteriolateral approach. An incision is made in the patient's back and the intervertebral disc between the vertebrae $V_S$, $V_I$ is removed. The first W-shaped spring 232 is implanted on one lateral side of the spinal cord, generally in a direction substantially parallel to the sagital plane $S_p$ and the second W-shaped spring 234 is implanted in a direction generally parallel to the sagital plane $S_p$ on the opposite side of the cord C. The first and second W-shaped springs 232, 234 are implanted such that the first inflection 241, third inflection 245, fourth inflection 249 and sixth inflection 253, respectively, lead into the disc space. In the implanted position, the first, third, fourth, and sixth inflections 241, 245, 249, 243 are positioned proximate an anterior aspect of the vertebrae $V_S$, $V_I$ and the trailing ends of the first and second W-shaped springs 232, 234 are positioned on a posterior cortical ring of the vertebral bodies of the superior and inferior vertebrae $V_S$, $V_I$.

In the implanted position, the first and second W-shaped springs 232, 234 are able to react to anatomical loads encountered by the spine and permit motion in six degrees of freedom between the superior and inferior vertebrae $V_S$, $V_I$. Specifically, the implanted first and second W-shaped springs 232, 234 permit lateral movement, vertical movement, movement along the sagittal plane $S_p$, and twisting about lateral, vertical and anterior to posterior axes. The six degrees of freedom of motion is able mimic anatomical motions permitted between the superior and inferior vertebrae $V_S$, $V_I$ when a healthy disc is positioned therebetween. This range of motion may permit more anatomical motion at facets F of the vertebrae $V_S$, $V_I$ in the implanted position.

It will be appreciated by those skilled in the art that changes could be made to the embodiments described above without departing from the broad inventive concept thereof. It is understood, therefore, that the invention is not limited to the particular embodiments disclosed, but it is intended to cover modifications within the spirit and scope of the present invention as defined by the claims below.

We claim:

1. An intervertebral implant for mounting between a superior vertebra and an inferior vertebra, the intervertebral implant comprising:

a first endplate having a first leading end, a first trailing end, a first lateral side, a second lateral side, a first vertebra engagement surface and a first inner surface, the first vertebra engagement surface mounted to the superior vertebra in an implanted position;

a second endplate having a second leading end, a second trailing end, a third lateral side, a fourth lateral side, a second vertebra engagement surface and a second inner surface, the second vertebra engagement surface mounted to the inferior vertebra in the implanted position; and an inlay mounted to and between the first and second inner surfaces in an assembled configuration, the inlay including a first mounting plate, a second mounting plate, a first W-shaped spring and a second W-shaped spring discrete from the first W-shaped spring, the first and second W-shaped springs mounted between the first and second mounting plates on opposite sides of an insertion axis, the first and second W-shaped springs having respective leading ends, trailing ends, and central axes that extend from the leading ends to the trailing ends, wherein the central axes are oriented generally parallel to the insertion axis.

2. The intervertebral implant of claim 1 wherein the first inner surface defines a first cavity and the second inner surface defines a second cavity, the first mounting plate positioned in the first cavity and the second mounting plate positioned in the second cavity in the assembled configuration.

3. The intervertebral implant of claim 1 wherein the first and second W-shaped springs include first, second, third and fourth legs, the first, second, third and fourth legs having a leg width and a leg thickness.

4. The intervertebral implant of claim 3 wherein the leg width is approximately one to four millimeters (1-4 mm) and the leg thickness is approximately two tenths to eight tenths millimeters (0.2-0.8 mm).

5. The intervertebral implant of claim 3 wherein the first legs are mounted to the first mounting plate and the fourth legs are mounted to the second mounting plate.

6. The intervertebral implant of claim 3 wherein the first and second legs define a first inflection, the second and third legs define a second inflection and the third and fourth legs define a third inflection.

7. The intervertebral implant of claim 6 wherein the first, second and third inflections include a stiffening member.

8. The intervertebral implant of claim 1 wherein the first and second W-shaped springs are constructed of a metallic material.

9. The intervertebral implant of claim 1 further comprising:

a first keel extending from the first vertebra engagement surface generally coplanar with the insertion plane; and a second keel extending generally perpendicularly from the second vertebra engagement surface generally coplanar with the insertion plane.

10. The intervertebral implant of claim 9 wherein the first and second keels have serrated teeth positioned on their top surfaces.

11. The intervertebral implant of claim 1 further comprising:

a plurality of spikes extending from the first and second vertebra engagement surfaces, the plurality of spikes positioned within endplates of the superior and inferior vertebra, respectively, in the implanted position.

12. An intervertebral implant system for mounting between a superior vertebra and an inferior vertebra defining a sagittal plane via a posterior approach generally parallel to the sagittal plane, the intervertebral implant system comprising:

a first W-shaped spring having first, second, third and fourth legs, the first leg having a first vertebra engagement surface and the fourth leg having a second vertebra engagement surface, the first and second vertebra engagement surfaces facing away from each other, the second leg extending from the first leg to the third leg, and the third leg extending from the fourth leg to the second leg, such that the first W-shaped spring has a first stiffening member positioned at a first inflection defined by the first and second legs, and the second and third legs attach to each other at a second inflection, wherein the first W-shaped spring has a first length, a first width and a first thickness, the first length being greater than the first width and the first width being greater than the first thickness, a length of the first, second and third legs being generally equal to the first length;

a second W-shaped spring discrete from the first W-shaped spring, the second W-shaped spring having fifth, sixth, seventh and eighth legs, the fifth leg having a third vertebra engagement surface and the eighth leg having a fourth vertebra engagement surface, the sixth leg extending from the fifth leg to the seventh leg, and the seventh leg extending from the eighth leg to the sixth leg, such that the sixth and seventh legs attach to each other at a third inflection, the third and fourth vertebra engagement surfaces facing away from each other, the second W-shaped spring having a second length, a second width and a second thickness, the first and third vertebra engagement surfaces contacting the superior vertebra and the second and fourth vertebra engagement surfaces contacting the inferior vertebra in an implanted position.

13. The intervertebral implant system of claim 12 wherein the first, second, third and fourth vertebra engagement surfaces have fixation mechanisms extending therefrom.

14. The intervertebral implant system of claim 13 wherein the fixation mechanisms are comprised of spikes.

15. The intervertebral implant system of claim 12 wherein the first W-shaped spring defines a first longitudinal axis and the second W-shaped spring defines a second longitudinal axis, the first and second longitudinal axes being oriented generally parallel to the sagittal plane in the implanted position.

16. The intervertebral implant system of claim 12 wherein a length of the fifth, sixth, seventh and eighth legs is generally equal to the first length and the second length.

17. The intervertebral implant system of claim 12, wherein the second inflection defines a second stiffening member, the intervertebral implant system further comprising:

a third stiffening member located at a fourth inflection defined by the third and fourths legs, the first and third stiffening members positioned proximate a leading end of the first W-shaped spring and the second stiffening member positioned proximate a trailing end of the first W-shaped spring.

* * * * *